United States Patent [19]

Hart

[11] Patent Number: 4,946,156
[45] Date of Patent: Aug. 7, 1990

[54] ORTHOSES OR PROSTHESES FOR COORDINATING LIMB MOVEMENT

[75] Inventor: David Hart, Keighley, England

[73] Assignee: Steeper (Orthopidic) Limited

[21] Appl. No.: 211,474

[22] Filed: Jun. 24, 1988

[30] Foreign Application Priority Data

Jun. 24, 1987 [GB] United Kingdom ............... 8714739
Aug. 20, 1987 [GB] United Kingdom ............... 8719672
Jan. 28, 1988 [GB] United Kingdom ............... 8801894

[51] Int. Cl.$^5$ ............................................ A63B 23/04
[52] U.S. Cl. ................................. 272/70; 128/80 F; 623/27
[58] Field of Search ............. 272/70; 128/80 R, 80 G, 128/80 F, 80 C, 88; 623/27, 30, 31, 32, 39, 40, 41, 42

[56] References Cited

U.S. PATENT DOCUMENTS

| | | | |
|---|---|---|---|
| 2,573,347 | 10/1951 | Mazzola | 623/41 X |
| 3,453,663 | 7/1969 | Minor | 623/40 |
| 4,456,003 | 6/1984 | Allard et al. | 128/80 F |
| 4,602,627 | 7/1986 | Vito et al. | 128/80 F |
| 4,632,096 | 12/1986 | Harris | 128/50 C X |
| 4,697,808 | 10/1987 | Larson et al. | 623/27 X |

FOREIGN PATENT DOCUMENTS

| | | | |
|---|---|---|---|
| 84712 | 6/1921 | Fed. Rep. of Germany | 623/27 |
| 0664650 | 5/1979 | U.S.S.R. | 623/27 |

*Primary Examiner*—Richard J. Apley
*Assistant Examiner*—H. N. Flaxman
*Attorney, Agent, or Firm*—Kinzer, Plyer, Dorn, McEachran & Jambor

[57] ABSTRACT

A reciprocating gait orthosis or prosthesis to provide a natural and efficient method of ambulation for paraplegic patients comprises hip joints which are coupled by a single push/pull member in the form of an inner metal cable which is surrounded by two nylon tubes, the outer nylon tube being a tight fit on the inner nylon tube which, in turn, closely embraces the inner metal cable so that they all move together, the arrangement also comprising two limb members each having a respective hip joint at one end and a respective knee joint at the other end with the joints rotatably coupling the limb member to further members which are pivotally coupled to a tie rod whereby rotation of the further members relative to the limb member about the joints is coordinated by the tie rod, there also being a spring which acts to urge the arrangement into a standing position and controls movement into a sitting position.

11 Claims, 7 Drawing Sheets

ORTHOSES OR PROSTHESES FOR COORDINATING LIMB MOVEMENT

FIELD OF THE INVENTION

The present invention, in some aspects, relates to prostheses or orthoses for assisting limb movement in a paraplegic person or in a person with a disabled or missing limb. The present invention also relates, in another aspect, to a device useful in such an orthosis or prosthesis.

One aspect of the present invention relates to a reciprocating gait orthosis.

DESCRIPTION OF THE PRIOR ACT

The Louisiana State University Reciprocating Gait Orthosis (LSURGO), as known, comprises means which couple a left and a right leg brace together in such a way that hip flexion in either one tends to force the other hip joint into extension, thereby providing a co-ordinating motion of the legs making possible a reciprocating gait. Each leg brace includes a pivotal joint at the hip, and the two hip joints are coupled by two cables.

An interconnected limb arrangement having two artificial limbs interconnected by two cables to coordinate the movement of the limbs is also known from GB-A-No. 1188647 (Hartley).

Whilst the LSURGO works well, the use of two cables makes for complication in the manufacture of the orthosis.

SUMMARY OF THE INVENTION

According to one aspect of the present invention, there is provided a reciprocating gait orthosis wherein the hip joints are coupled by a single push/pull member.

Another aspect of the present invention comprises a push/pull member in the form of an inner cable and two tubes, one within the other, which all move together. Such a member is used in a preferred embodiment of the reciprocating gate orthosis.

A further aspect of the present invention relates to an orthosis or prosthesis which co-ordinates, and assists, movement between two parts of the same limb. The further aspect relates for example to assisting the paraplegic or disabled person in moving between sitting and standing postures.

Many different arrangements are known which include a spring or other elastic or resilient device associated with an artificial knee joint to assist straightening of an artificial leg, or to assist in straightening the leg of a disabled person, but the known arrangements operate only on or across the single knee joint. Examples of such arrangements include GB-A-No. 2004753 (Blatchford) and GB-A-No. 813501 (Cresswell).

According to the further aspect of the present invention, there is provided an orthosis or prosthesis for coordinating movement about two joints of the same limb, comprising a limb member having pivotal joints at respective ends thereof joining the limb member to further members, a coordination member pivotally coupled to the further members for coordinating rotation of one of the further members about one of the joints with rotation of the other of the further members about the other joint, and resilient means which urges the orthosis or prosthesis into a particular configuration.

BRIEF DESCRIPTION OF THE DRAWINGS

For a better understanding of the present invention, reference will now be made by way of example to the accompanying drawings, in which.

DESCRIPTION OF THE PREFERRED EMBODIMENTS

Figure 1:
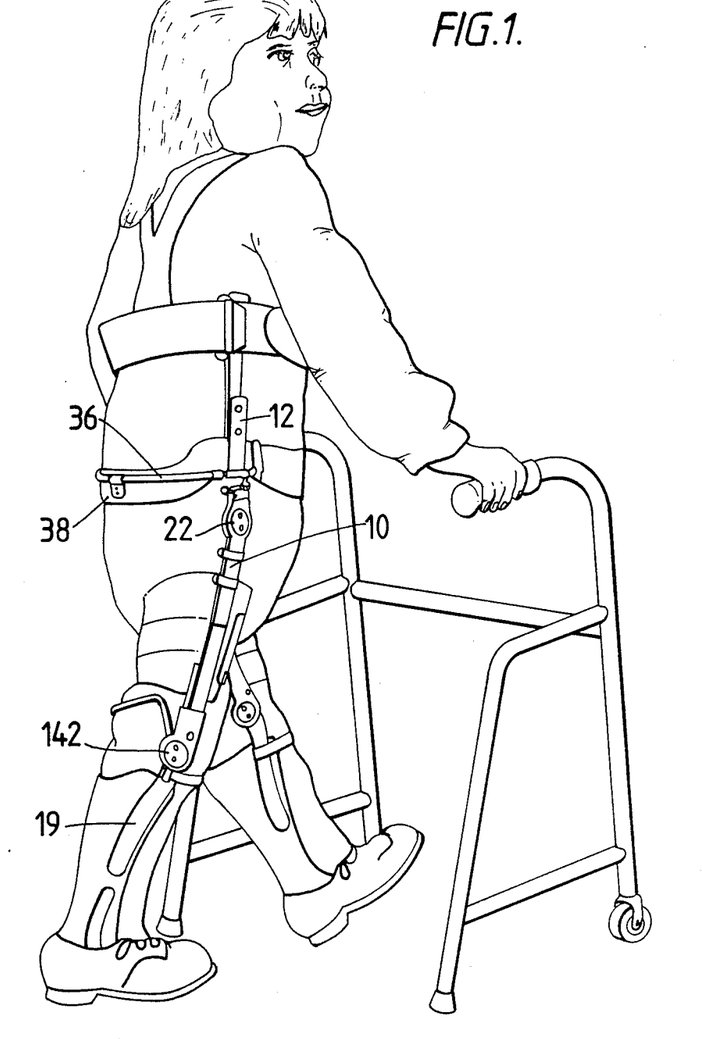
FIG. 1 is a perspective view of an illustrative orthosis according to the invention fitted to a paraplegic patient.
Figures 5, 8:
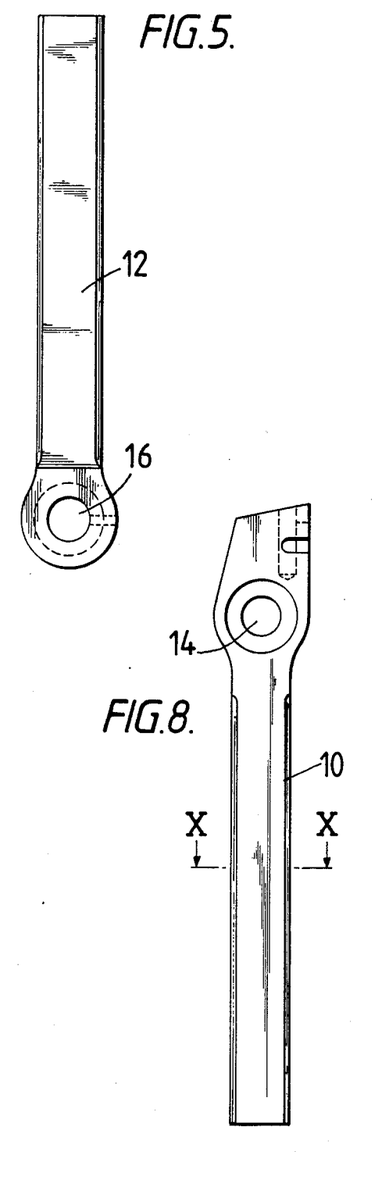
FIG. 5 is a front elevation of a steel provided in one of the leg braces.
FIG. 8 is a front view of another part of one of the leg braces.
Figures 6, 7, 9, 10:
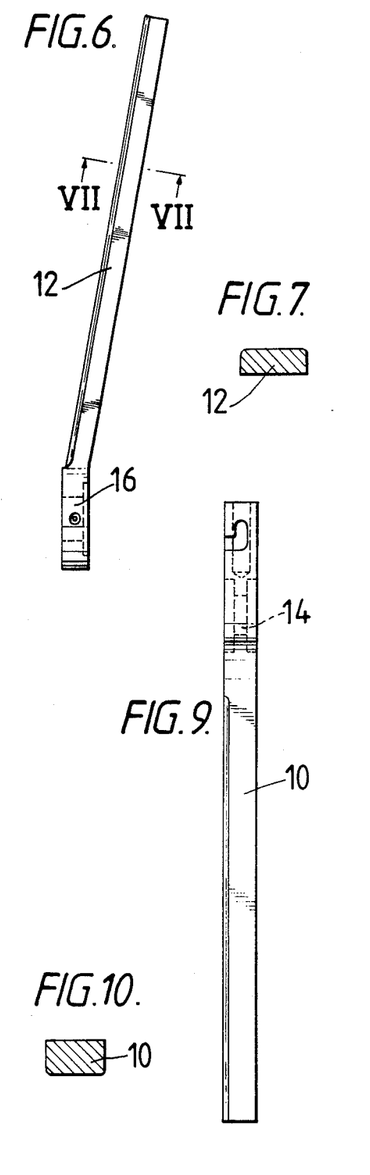
FIG. 6 is a side elevation of the steel shown in FIG. 5.
FIG. 7 is a sectional view taken on the line VII—VII in FIG 6.
FIG. 9 is a side view of the part shown in FIG. 8.
FIG. 10 is a sectional view taken on the line X—X in FIG. 8.
Figure 15:
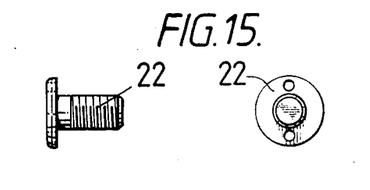
FIG. 15 is a sectional view and an end view respectively of a bearing screw incorporated into the orthosis of FIG. 1.
Figure 16:
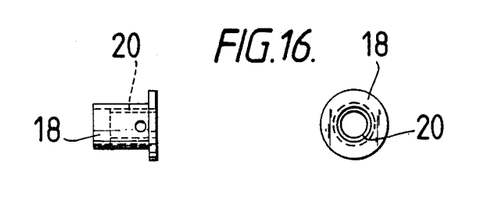
FIG. 16 is a side view and an end view respectively of a hub provided in the orthosis of FIG. 1.

The illustrated reciprocating gait orthosis of FIG. 1 comprises left and right leg braces which include lower steels 10—see FIGS. 8 to 10—and upper steels 12—see FIGS. 5 to 7—each of which are provided with respective eyelets 14, 16 through which a hub 18 passes—see FIG. 16—so that the upper and lower steels are pivoted together. The hub is internally screw-threaded at 20 so as to receive a screw-threaded bush or bearing screw 22—see FIG. 15. The hub 18 passes through roller thrust races 21 in the steel 10 which bear outwardly against a hardened steel bush and the head of the screw 22 and inwardly against hardened steel washers 25.

Figure 11:
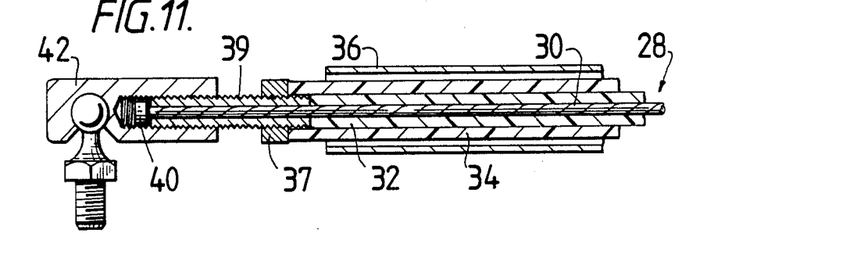
FIG. 11 is a sectional view through part of the push-/pull member and its associated parts.

Each hub 18 and its respective bearing screw 22 together form a hip joint pivotally connecting the upper and lower steels. The two hip joints are arranged one on each side of the patient. The two lower steels are coupled together by a single push/pull member 28, one end of which is best shown in FIG. 11, the other end being identical. The push/pull member 28 moves with clearance within a tubular steel carrier 36 fixed to a back band 38.

Figure 12:
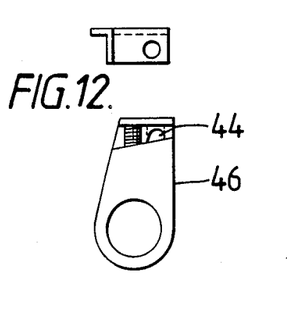
FIG. 12 is a front view of a locking mechanism forming part of the orthosis shown in FIG. 1.
Figure 13:
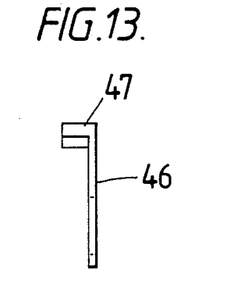
FIG. 13 is a side view of the part shown in FIG. 12.
Figure 14:
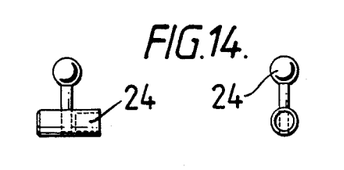
FIG. 14 shows a front view and a side view respectively of a locking member forming part of the locking mechanism.

Each lower steel 10 can be uncoupled from the push-/pull member and thus from the other lower steel by a locking plunger 24 and catchplate 46—see FIGS. 12 to 14. As will be seen from FIG. 4, this locking plunger is loaded by a spring 26. The spring 26 urges the plunger upwardly into a recess 44 in a catch plate 46: —see FIGS. 12 and 13. The catch plate 46 is interposed between the steels around the bush 23. The plate 46 has a head 47 which bears against an inclined end surface of the steel 10 when the plunger locks the steel to the plate. When unlocked, the plate 46 can rotate anticlockwise (as viewed in FIG. 2) with respect to the lower steel 10.

The push/pull member comprises an inner metal cable 30 which is surrounded by two nylon tubes 32 and 34. The outer nylon tube 34 is a tight fit on the inner nylon tube 32, and the inner nylon tube closely embraces the metal inner cable 30 so that they can all move together.

The cable has a ferrule 40 at its end. Between the ferrule and the inner tube 32 is an externally threaded metal tube 39 through which the cable passes. The metal tube extends into the outer tube and an adjusting nut 37 threaded on the metal tube bears against the end of the outer tube 34 to take any play out of the outer tube. A ball joint 42 is threaded onto the tube 39. The ball joint is also attached to the upper end of the lower steel 10 - see FIGS. 3 and 4. It thus follows that a walking movement of one leg brace causes the other leg brace to move in the opposite direction due to their connection by the push/pull member 28.

It will thus be seen that the reciprocating gait orthosis illustrated in FIGS. 1 to 16 is of comparatively simple construction which means that it is easier and cheaper to produce and does not give rise to problems in use by the patient.

Figure 17:
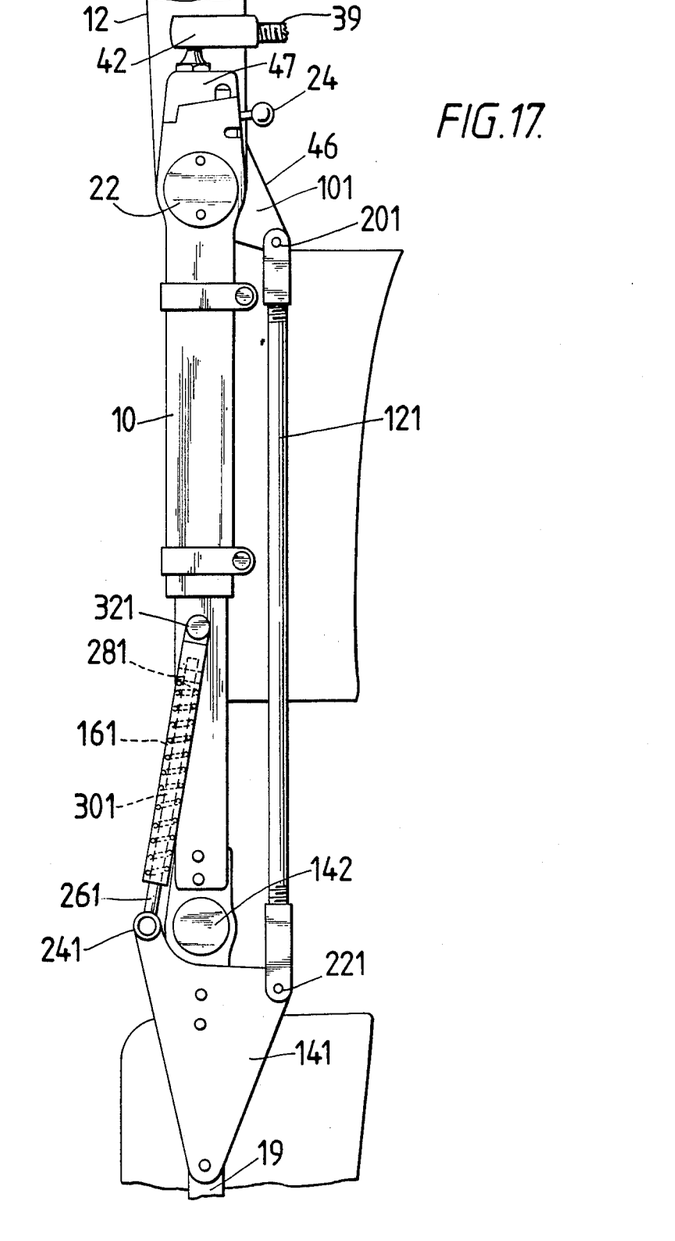
FIG. 17 is a partial assembly side view of a modification of the orthosis shown in FIG. 1.

FIG. 17 shows an illustrative "up-and-down" orthosis or prosthesis which assists a paraplegic patient or one with a disabled or missing limb, hand or foot to sit down from a standing posture and to rise from a sitting posture. The orthosis of FIG. 17 is shown, illustratively, as a modification of the reciprocating gait orthosis of FIGS. 1 to 16. It will be appreciated, however, that it is inventive in its own right, the concept embodied in the orthosis of FIG. 17 being applicable more generally than in just a reciprocating gait orthosis.

Figure 2:
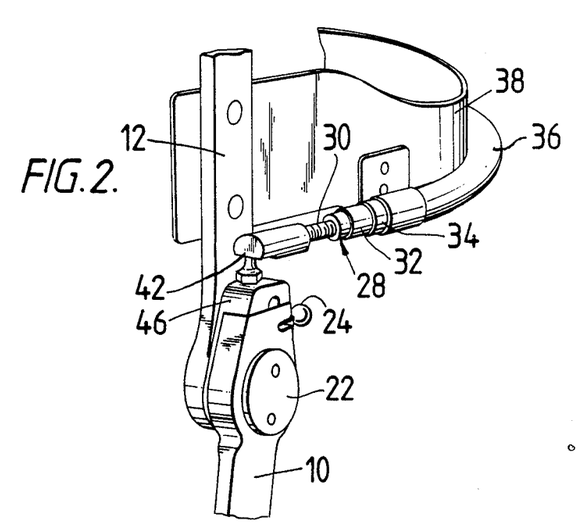
FIG. 2 is a fragmentary detailed perspective view of part of the leg brace shown in FIG. 1.
Figure 3:
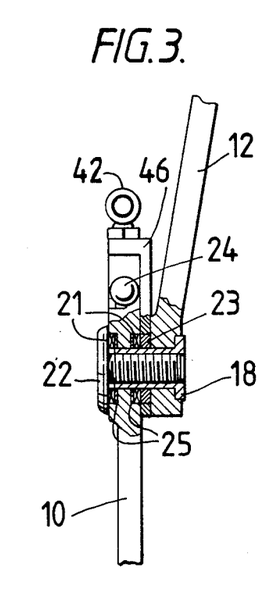
FIG. 3 is a fragmentary detailed view, partly in section, of an upper part of one of the leg braces.
Figure 4:
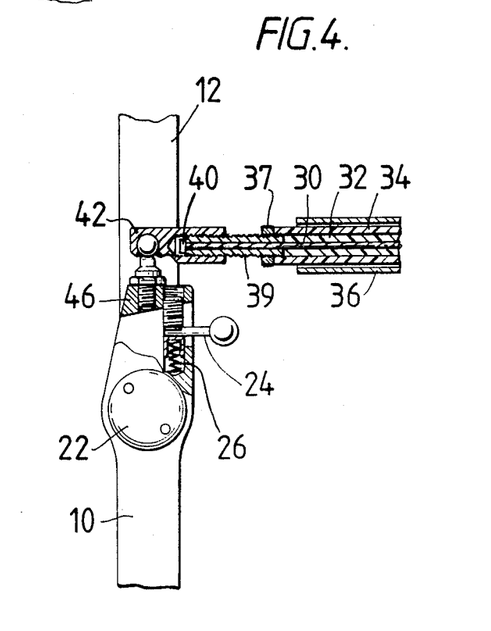
FIG. 4 is a fragmentary detailed view, partly in section, of the part shown in FIG. 3 but at right-angles thereto.

The orthosis shown in FIG. 17 comprises the upper steel 12, the lower steel 10 and a lower leg steel 19 similar to those shown in FIG. 1. The upper and lower steels 12,10 are pivotally coupled by a hip joint as shown in FIGS. 2 to 4 except for a modification to the catch plate 46 which in FIG. 17 has an extension or top lever 101 which is either formed on or attached to the catch plate 46. The lower leg steel 19 is coupled to the lower steel 10 by a knee joint 142.

Pivotally connected at 201 to the outer extremity of the top lever 101 and depending therefrom is a hip-to-knee tie rod 121 which has its lower end pivotally connected at 221 to a lower plate 121 which can be formed on or be attached to the lower leg steel 19 below the knee joint 142 of the orthosis. Pivotally connected to the lower plate 141 at 241 is a rod 25 which extends into a spring housing 161 and which has an adjusting nut 281 at its inner end to adjust the compression of a helically-coiled spring 301. The upper end of the spring housing 161 is pivotally connected to the lower steel 10 of the orthosis at 321.

The hip joint, lower steel 10, knee joint 142, lower plate 141, top lever 101 and the tie rod 121 pivotally connected to plate 141 and lever 101 form a parallelogram arrangement which coordinates movement about the hip joint with movement about the knee joint. The spring 301 acts to hold the parallelogram in the position corresponding to the standing position of the user.

When a user wishes to sit, the plunger 24 is moved to release the lower steel 10 from the catch plate. The catch plate can then rotate relative to the lower steel about the hip joint. The tie rod 121 then pulls upwardly on the lower plate 141 rotating the knee joint and compressing the spring 301. Thus assistance is given to a patient in sitting down from a standing posture in that the spring controls the patients descent. The spring thus also assists in rising up from a sitting posture.

The spring 301 and its housing 161 can take many different forms. It could, for example, be replaced by elastic or by a tension spring arranged above the nut 28. A compression spring is, however, safer. The spring and its housing could be positioned in the parallelogram in positions other than the one shown in FIG. 17.

The construction shown in FIG. 17 eliminates the need for a knee lock when standing because the lock 24 between the catch plate and the lower steel, together with rod 121, locks the knee.

FIGS. 18 to 24 show a modification of the orthosis shown in FIG. 17.

In the orthosis of FIGS. 18 to 24 the tie rod 121 takes the form of, or is replaced by, a Bowden cable 342 or the like and a catch 282,382,402 is provided to hold the relatively movable parts 10,19 of the orthosis or prosthesis in two or more specific positions.

Figure 18:
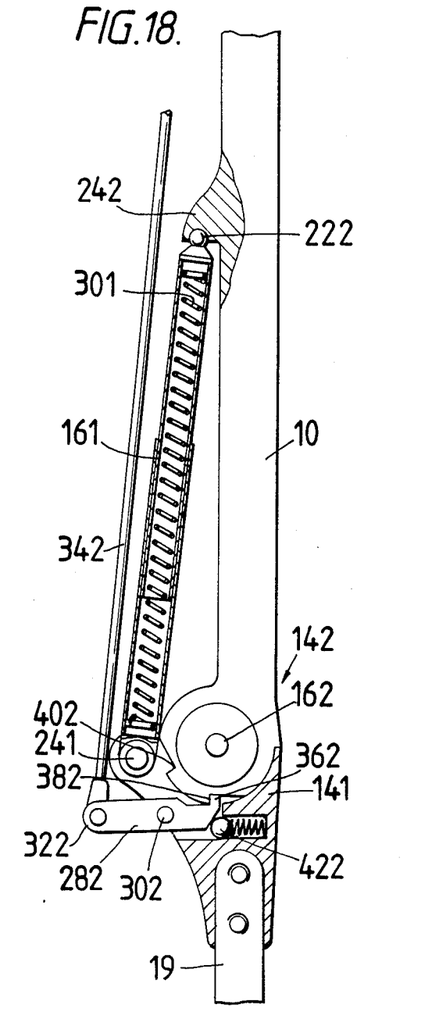
FIG. 18 is a part-sectional view of part of the orthosis shown in FIG. 17.
Figure 19:
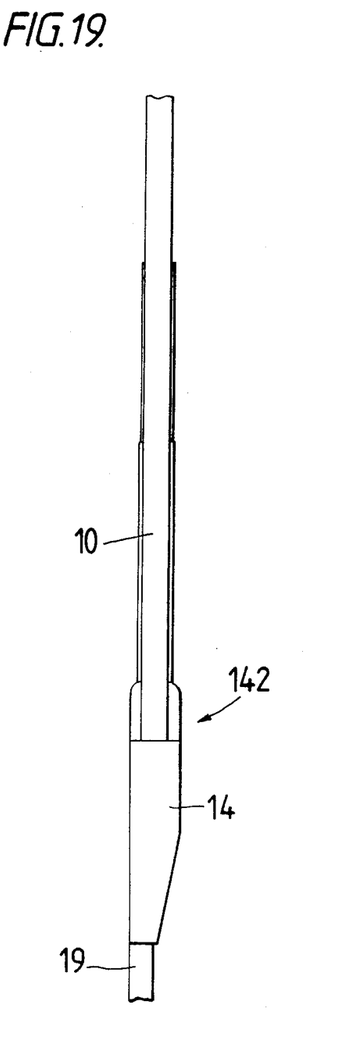
FIG. 19 is a side view of what is shown in FIG. 18.
Figure 20:
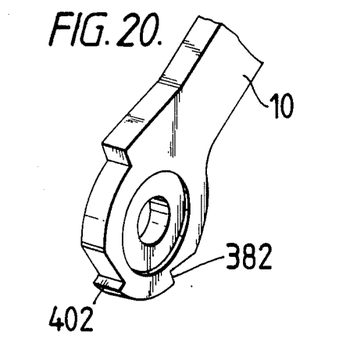
FIG. 20 is a fragmentary detailed perspective view of a steel used in the orthosis of FIG. 17.

The orthosis illustrated in FIG. 18 comprises the lower steel 10, the lower leg steel 19 and the knee joint 142 by which the lower and lower leg steels 10,19 can pivot with respect to each other.

The spring 301 and its housing 161 are in the form of a telescopic assembly 18 pivotally connected at its lower end 241 to the lower plate 141 and is provided with a ball joint connection 222 at its upper end with a projection 242 on the lower steel 10. The coiled compression spring 301 within the telescopic assembly 18 serves to urge the knee joint 142 into a position where the lower leg steel 19 is substantially in alignment with the lower steel 10. In FIG. 18, the lower plate is an integral part of the knee joint 142.

A catch lever 282 is pivotally mounted at 302 on the lower plate 141 and is provided at its outer end 322 with a pivotal connection for the Bowden cable 342. The inner end of the lever 282 is in the form of a nose 362 which engages oppositely facing, spaced apart, first and second shoulders 382 and 402 formed on the lower end of the lower steel 10. Disengagement of the catch nose 362 from the first shoulder 382 allows the lower leg steel 19 to move angularly about the knee joint 142 with respect to the upper steel 10.

The second shoulder 402 on the lower end of the upper steel 10 can likewise be engaged by the catch nose 36. Such engagement takes place when the lower leg steel 19 has moved to a position where it is approximately at right angles to the lower steel 10. This corresponds to a sitting posture of the person using the orthosis.

A spring-loaded ball 422 acts on one end of the catch lever 282 in such a way as to urge the catch nose upwards into engagement with the shoulders.

The upper end of the cable 342 is attached to the top lever 101 of the catch plate 46.

When the user wishes to sit, from a standing position, the catch plate 46 is released from the lower steel 10 as described above. Rotation of the catch plate by the user, then pulls on the cable 342 releasing the catch lever 282 from shoulder 382 and also assisting rotation of the lower leg steel 19 about the knee joint 142 against the spring 301 which thus controls the user's descent. The lever engages the shoulder 402 and prevents the spring from straightening the leg. When standing from a sitting position the user moves to pull on the cable 342 to release the lever 282 from shoulder 402 and so, the spring assists the ascent. The cable 342 coordinates movement about the hip joint with movement about the knee joint.

Figures 21, 22:
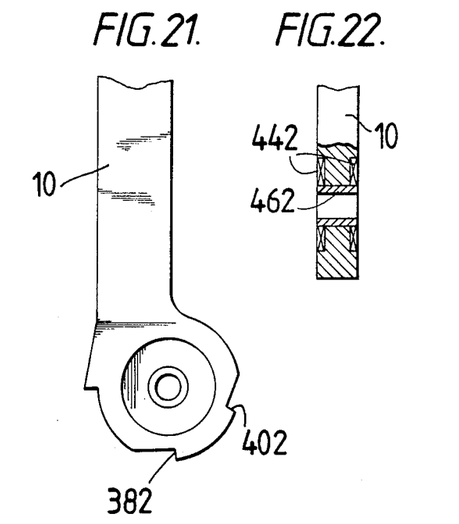
FIG. 21 is a front view of the part shown in FIG. 20.
FIG. 22 is a section through the parts shown in FIGS. 20 and 21.
Figure 23:
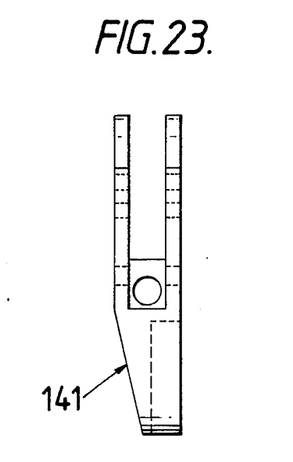
FIG. 23 is a side view of a plate forming part of the orthosis shown in FIG. 17.
Figure 24:
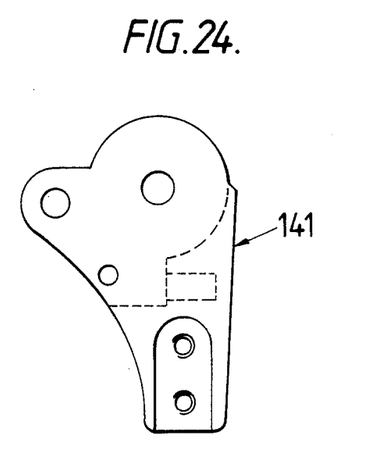
FIG. 24 is a front view of the part shown in FIG. 23.

FIGS. 19 to 24 show details of the orthosis: it will be noted from FIG. 22 in particular that the knee joint 142 at the lower end of the lower steel 10 includes roller thrust bearings 442 and a radial roller bearing 462. Such a joint may be used in the orthosis of FIG. 17.

Although the invention has been illustrated by reference to an orthosis, it may be applied also to a prosthesis.

I claim:

1. A reciprocating gait orthosis or prosthesis comprising,
   a left leg member and a right leg member adapted to be secured to a user's legs or replace a user's missing legs, wherein said leg members include a pivotal hip joint at the upper end of each leg member,
   means of coordinating the movement of said leg members, wherein said coordinating means consists of a single push/pull member coupled to each leg member by respective releasable coupling means,
   said coupling means comprise a pivotable member connected to the push/pull member and locking means for releasably locking the associated leg member to the pivotable member, wherein the pivotable member is arranged to pivot about its associated hip joint.

2. An orthosis or prosthesis according to claim 1 wherein the push/pull member is connected to ball joints at the upper ends of the leg members.

3. An orthosis or prosthesis according to claim 1 wherein the push/pull member takes the form of an inner metal cable and two tubes, one within the other, which all move together.

4. An orthosis or prosthesis according to claim 3 wherein the outer tube is a tight fit on the inner tube, while the inner tube closely embraces the inner metal cable.

5. An orthosis or prosthesis according to claim 3 wherein the tubes are made of nylon.

6. An orthosis or prosthesis according to claim 1 wherein the push/pull member is slidably arranged within a tubular guide.

7. An orthosis or prosthesis according to claim 1 wherein pivotal joints are provided at the lower ends of the leg members for the pivotal connection thereto of lever members, there being a coordination member coupled to the lever members for coordinating rotation of the lever members about their respective pivotal connections.

8. An orthosis or prosthesis according to claim 7 wherein yielding means connect each lever to the respective leg member so as to urge the orthosis or prosthesis into a desired configuration.

9. An orthosis or prosthesis according to claim 7 wherein the coordination member is a tie rod.

10. An orthosis or prosthesis according to claim 7 wherein the coordination member comprises a cable.

11. An orthosis or prosthesis according to claim 7 wherein the coordination member is coupled to the respective lever by a further lever which is releasably engageable with the associated pivotal connection to lock the pivotal connection.

* * * * *